(12) United States Patent
Lu

(10) Patent No.: US 7,563,764 B2
(45) Date of Patent: Jul. 21, 2009

(54) ANTIMICROBIAL PEPTIDES BASED ON TRIPEPTIDE REPEATS

(75) Inventor: Helen S. M. Lu, Wallingford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 136 days.

(21) Appl. No.: 11/311,387

(22) Filed: Dec. 19, 2005

(65) Prior Publication Data

US 2006/0166883 A1 Jul. 27, 2006

Related U.S. Application Data

(60) Provisional application No. 60/640,591, filed on Dec. 30, 2004.

(51) Int. Cl.
*A61K 38/00* (2006.01)
*C07K 2/00* (2006.01)

(52) U.S. Cl. .......................... 514/2; 530/300; 530/333; 530/345

(58) Field of Classification Search .................. None
See application file for complete search history.

(56) References Cited

U.S. PATENT DOCUMENTS

| | | | | |
|---|---|---|---|---|
| 4,966,848 A * | 10/1990 | Smith et al. | ................. | 435/193 |
| 5,223,421 A * | 6/1993 | Smith et al. | ................. | 435/193 |
| 5,515,117 A * | 5/1996 | Dziabo et al. | ........... | 351/160 H |
| 5,639,726 A * | 6/1997 | Lawrence et al. | ............. | 514/12 |
| 5,652,211 A * | 7/1997 | Porro | ......................... | 514/11 |
| 5,837,218 A * | 11/1998 | Peers et al. | ................ | 424/1.69 |
| 5,847,047 A | 12/1998 | Haynie | | |
| 7,091,185 B2 * | 8/2006 | Strom et al. | ................... | 514/18 |
| 2004/0072992 A1 * | 4/2004 | Machida et al. | ............. | 530/327 |

OTHER PUBLICATIONS

Iwata T. et al. "Design and Synthesis of Amphipathic 3(10)-Helical Peptides and Their Interactions with Phospholipid Bilayers and Ion Channel Formation" 1994, J. Biol. Chem. vol. 269, pp. 4928-4933.*
U.S. Appl. No. 60/496,122, filed Aug. 18, 2003, Keeler et al.
Michael Zasloff, Antimicrobial Peptides of Multicellular Organisms, Nature, 2002, pp. 389-395, vol. 415.
Richard M. Epand et. al., Diversity of Antimicrobial Peptides and Their Mechanisms of Action, Biochimica et Biophysica Acta, 1999, pp. 11-28, vol. 1462.
Sannamu Lee et. al., Relationship Between Antimicrobial Activity and Amphiphilic Property of Basic Model Peptides, Biochim. Biophys. Acta, 1986, pp. 211-219, vol. 862.
Lars Anderson et. al., Large-Scale Synthesis of Peptides, Biopolymers (Peptide Science), 2000, pp. 227-250, vol. 55.
R.B. Merrifield, Solid Phase Peptide Synthesis/The Synthesis of a Tetrapeptide, J. Am. Chem. Soc., 1982, pp. 2149-2154, vol. 85.
Marketa Rinnova et. al., Solid-Phase Peptide Synthesis by Fragment Condensation: Coupling in Swelling Volume, Lett. Peptide Science, 1999, pp. 15-22, vol. 6.
Bun-Ichiro Nakajima et al., Polymerization of L-Alanylglycine With Diphenylphosphoryl Azide, Polymer Journal, 1981, pp. 183-189, vol. 13.
Mukund V. Deshpande, Ethanol Production From Cellulose Coupled Saccharification/Fermentation Using *Saccharomyces cerevisiae* and Cellulase Complex From Sclerotium Rolfsii UV-8 Mutant*, Applied Biochemistry and Biotechnology, vol. 36:227-234, 1992.
J. -N. Zeng et al., The Synthesis of Poly-L-Amino Acids and Their Characterization by Size Exclusion Chromatography With Low-Angle Laser Light Scattering (SEC-LALLS/UV/DRI), Journal of Polymer Science: Part A: Polymer Chemistry, vol. 30:1809-1820, 1992.
Edward Bellion et al., Methylamine Utilization in Yeast and Bacteria: Studies Using in Vivo NMR, Microb. Growth C1 Compd., [Int. Symp. ], $7^{TH}$, 1993, 415-432, Editor(s): Murrell, J. et al., Publisher: Intercept, Andover, UK.
G. J. Sulter et al.,, Proliferation and Metabolic Significance of Peroxisomes in *Candida boidinii* During Growth on D-Alanine or Oleic Acid as the Sole Carbon Source, Arch. Microbiol., 153:485-489, 1990.

* cited by examiner

*Primary Examiner*—Andrew D Kosar
(74) *Attorney, Agent, or Firm*—Christine M. Lhulier

(57) ABSTRACT

The invention described herein relates to compositions of novel antimicrobial peptides that comprise hydrophobic and cationic residues, based on monomeric tri-peptide units. The peptides of the present invention exhibit high antibacterial activity and low hemolytic activity. The invention further provides compositions comprising these antimicrobial peptides and methods of use thereof for killing, reducing the growth of, or preventing the growth of microorganisms. The invention also provides antimicrobial substrates, medical devices, protective garments and barrier materials comprising the peptides of the present invention.

19 Claims, No Drawings

ANTIMICROBIAL PEPTIDES BASED ON TRIPEPTIDE REPEATS

This application claims the benefit of U.S. Provisional Application Ser. No. 60/640,591, filed Dec. 30, 2004.

FIELD OF THE INVENTION

This invention relates to cationic, antimicrobial oligopeptides, as well as methods of production and uses thereof. The antimicrobial peptides of the present invention are useful in pharmaceutical, healthcare, medical device, industrial, food, agricultural and personal care applications.

TECHNICAL BACKGROUND OF THE INVENTION

Antimicrobial peptides (AMPs) are ubiquitous in nature and play an important role in the innate immune system of many species (Zasloff, M., Nature (2002) 415:389-395; Epand, R. M., and Vogel, H. J., Biochim Biophys Acta (1999) 1462:11-28). Antimicrobial peptides are diverse in structure, function, and specificity. One major class of antimicrobial peptides consists of linear α-helical peptides, such as cecropin and magainin. Haynie (U.S. Pat. No. 5,847,047) described synthetic peptides based on a heptad repeat and comprised of Leu and Lys residues that were designed to adopt an α-helical amphiphilic structure (see, for example, SEQ ID NO:6); these peptides exhibited activity at 8-63 μg/mL against *Escherichia coli* and *Staphylococcus aureus* in solution, however they also exhibited moderate hemolytic activity. Lee, et al. (Biochim. Biophys. Acta (1986) 862:211-219) showed that peptides exhibiting α-helical conformations such as pentapeptide repeat (e.g., (Leu-Leu-Ala-Arg-Leu)$_3$) (SEQ ID NO:7) and tetrapeptide repeat (e.g., (Leu-Ala-Arg-Leu)$_3$ (SEQ ID NO:8) and (Leu-Ala-Arg-Leu)$_4$) (SEQ ID NO:9) peptides had potent antimicrobial activity. In contrast, tri-peptide repeat peptides such as (Ala-Arg-Leu)$_3$ (SEQ ID NO:10) and (Ala-Arg-Leu)$_4$ (SEQ ID NO:11) had weak or no antimicrobial activity.

A need exists for AMPs which exhibit both good antimicrobial activity and reduced hemolytic activity and that can be produced in a cost-effective manner. The present invention provides antimicrobial peptides based on tri-peptide units that exhibit potent antimicrobial activity and reduced hemolytic activity.

SUMMARY OF THE INVENTION

In one embodiment the present invention provides antimicrobial compositions comprising at least one antimicrobial oligopeptide comprised of monomeric tri-peptide units randomly selected at each position according to:

(XXZ or ZXX or XZX)$_n$      Formula (I):

wherein:
(a) X is a hydrophobic amino acid independently selected from the group consisting of Leu, Ile, Trp, Phe, Val, Met, and Ala, with the proviso that only one Ala residue is permitted per monomeric tri-peptide unit;
(b) Z is a cationic amino acid independently selected from the group consisting of Lys, Arg, His, Orn, Har, and Dab; and
(c) n=5 to 100.

For clarity, Applicants intend that at each tripeptide position of the oligopeptide, a tripeptide will be randomly selected from XXZ, ZXX and XZX.

In a second embodiment, the present invention provides antimicrobial compositions comprising at least one antimicrobial oligopeptide comprised of monomeric tri-peptide units according to:

(XXZ)$_n$;      Formula (II):

(ZXX)$_n$;      Formula (III): or (XZX)$_n$;      Formula (IV):

wherein:
(a) X is a hydrophobic amino acid independently selected from the group consisting of Leu, Ile, Trp, Phe, Val, Met, and Ala, with the proviso that only one Ala residue is permitted per monomeric tri-peptide unit;
(b) Z is a cationic amino acid independently selected from the group consisting of Lys, Arg, His, Orn, Har, and Dab; and
(c) n=5 to 100.

The present invention also provides a method for killing, inhibiting or preventing the growth of at least one microbe, the method comprising contacting the microbe with an effective amount of an antimicrobial composition, the antimicrobial composition comprising at least one antimicrobial oligopeptide of the invention. The antimicrobial oligopeptide comprises from about 0.00001% to about 20% by weight of the composition. In a preferred embodiment of the invention the antimicrobial peptide comprises from about 0.0001% to about 10% by weight of the composition. In a more preferred embodiment of the invention the antimicrobial peptide comprises from about 0.0001% to about 5% by weight of the composition.

In another embodiment, the invention provides an antimicrobial substrate comprising an antimicrobial composition bound to or incorporated into a substrate, wherein the antimicrobial composition is comprised of at least one antimicrobial oligopeptide of the invention. And further, the invention provides an article comprised of antimicrobial substrates of the invention.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The invention described herein provides novel antimicrobial oligopeptides based on monomeric tri-peptide units comprised of hydrophobic and cationic residues. The peptides of the present invention have high antibacterial activity and low hemolytic activity. The invention further provides compositions comprising these antimicrobial peptides and methods of use thereof for killing, reducing the growth of, or preventing the growth of microorganisms. The invention also provides substrates, medical devices, protective garments and barrier materials comprising the peptides of the present invention.

Definitions and Abbreviations:

In this disclosure, a number of terms and abbreviations are used. The following definitions are provided.

The terms "peptide", "oligopeptide" and "peptide oligomer" will be used interchangably and will refer to amino acid sequences of between three and one hundred amino acids in length. "Tri-peptide oligomers" are peptide oligomers comprised of monomeric tri-peptide units.

The term "polymer" refers to a macromolecule comprising a plurality of monomers, wherein the polymer may be comprised of conventional inorganic monomers to form polymers such as polyester and polyurethane, or may be comprised of organic monomers such as amino acids to form polymers such as oligopeptides and proteins.

The terms "monomeric tri-peptide unit" or "tri-peptide" refer to a single peptide unit comprising three amino acids.

The term "antimicrobial" means having to do with the killing, growth inhibition or growth prevention of microorganisms. "Growth inhibition" means reduced growth of the microorganisms. "Growth prevention" means that growth is stopped.

The term "microorganism" or "microbe" is meant to include any organism comprised of the phylogenetic domains bacteria and archaea, as well as unicellular and filamentous fungi (such as yeasts and molds), unicellular and filamentous algae, unicellular and multicellular parasites, and viruses.

The term "cytotoxic" means the killing or lysis of eukaryotic organisms.

The term "amphiphilic peptide" refers to a peptide with spatially segregated polar and non-polar residues.

The terms "amphiphilic helix" and "amphipathic helix" are used interchangably and mean any protein or peptide secondary structure that forms a helix wherein that helix includes both hydrophobic and hydrophilic regions and demonstrates an affinity for hydrophilic structures such as those found in lipid bilayers and cell membranes.

A "substrate coated with an effective amount of an antimicrobial composition" means applying to the surface a composition comprising one or more antimicrobial peptides in an amount effective to kill, inhibit or prevent the growth of microorganisms.

The term "MIC" refers to minimal inhibitory concentration and will be defined as the lowest concentration of either soluble peptide or peptide immobilized on a polymer that results in total kill of bacteria.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence.

The term "back-translate" refers to deducing the nucleotide sequence encoding a given amino acid sequence, taking into account organism-specific codon preferences, from a given amino acid sequence.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

"ATCC" refers to the American Type Culture Collection International Depository located at 10801 University Boulevard, Manassas, Va. 20110-2209, U.S.A. The "ATCC No." is the accession number to cultures on deposit with the ATCC.

"Orn", "Har" and "Dab" refer to ornithine, homoarginine and 2,4-diaminobutyric acid, respectively.

The present invention provides antimicrobial oligopeptides comprising monomeric tri-peptide units randomly selected at each position according to:

$$(XXZ \text{ or } ZXX \text{ or } XZX)_n \quad \text{(Formula I):}$$

wherein:
(a) X is a hydrophobic amino acid independently selected from the group consisting of Leu, Ile, Trp, Phe, Val, Met, and Ala, with the proviso that only one Ala residue is permitted per monomeric tri-peptide unit;
(b) Z is a cationic amino acid independently selected from the group consisting of Lys, Arg, His, Orn, Har, and Dab; and
(c) n=5 to 100.

The present invention also provides antimicrobial oligopeptides comprising monomeric tri-peptide units according to:

$$(XXZ)_n; \quad \text{Formula (II):}$$

$$(ZXX)_n; \quad \text{Formula (III): or}$$

$$(XZX)_n; \quad \text{Formula (IV):}$$

wherein:
(a) X is a hydrophobic amino acid independently selected from the group consisting of Leu, Ile, Trp, Phe, Val, Met, and Ala, with the proviso that only one Ala residue is permitted per monomeric tri-peptide unit;
(b) Z is a cationic amino acid independently selected from the group consisting of Lys, Arg, His, Orn, Har, and Dab; and
(c) n=5 to 100.

The peptides of Formulae (I) through (IV) may comprise L- or D-amino acids.

The antimicrobial peptides of Formulae (I) through (IV) may comprise an additional one to three uncharged or cationic amino acid residues at the N-terminus of the peptide, the C-terminus, or at both the N-terminus and C-terminus. The uncharged residues are selected from the group consisting of Gly, Leu, Ala, Ile, Trp, Ser, Thr, Met, Phe, Tyr, Asn, Gln and Val; in another embodiment the uncharged residues are Gly, Ala, Leu, Phe, Val and Met.

The antimicrobial peptides of Formulae (I) through (IV) may be modified on the N-terminus with an acetyl group, modified on the C-terminus with an amide, or combinations thereof. In addition, the antimicrobial peptides of Formulae (I) through (IV), modified with one to three uncharged or cationic amino acid residues at the N-terminus of the peptide, the C-terminus, or at both the N-terminus and C-terminus, may also be further modified on the N-terminus with an acetyl group, modified on the C-terminus with an amide, or combinations thereof.

In one embodiment of the invention, the hydrophobic residues in Formulae (I) through (IV) are selected from the group consisting of Leu, Phe, Ala, Ile, and Val. In another embodiment of the invention, the cationic residues are selected from the group consisting of Lys and Arg. In still another embodiment of the invention, the hydrophobic residues in Formulae (I) through (IV) are selected from the group consisting of Leu, Phe, Ala, Ile, and Val, and the cationic residues are selected from the group consisting of Lys and Arg.

The preferred oligopeptides of the present invention are comprised primarily of hydrophobic residues, such as leucine and valine, and cationic residues, such as lysine. tri-peptide In one embodiment of the invention, oligopeptides are comprised of n=5 to 100 monomeric tri-peptide units. In another embodiment of the invention, n=5 to 50 monomeric tri-peptide units. In still another embodiment of the invention, n=5 to 10 monomeric tri-peptide units. In an additional embodiment of the invention, the hydrophobic residues of the oligopeptide are selected from the group consisting of Leu, Phe, Ala, Ile, and Val, the cationic residues are Lys or Arg, and n=5 to 10. Preferred oligopeptides of the invention include, but are not limited to, SEQ ID NOs: 2, 3 and 5.

The peptides of the invention may be synthesized by solid-phase synthesis, solution-phase synthesis or recombinant biosynthesis.

Solid-Phase and Solution-Phase Synthesis

The tri-peptide oligomers described in the present invention have the advantage of simplicity of sequence, while preserving potent antimicrobial activity and low hemolytic activity. The synthesis of peptides based on monomeric tri-peptide units allows for large scale synthesis by standard methods that are well known in the art (see, for example, Andesson, et al. Biopolymers (Peptide Science), (2000) 55: 227-250). For example, the peptides may be synthesized by solid-phase synthesis as originally described by Merrifield (J. Am. Chem. Soc. (1982) 85:2149-2154), or by Stewart (Solid Phase Peptide Synthesis ($2^{nd}$ ed); Pierce Chemical Company, Rockford, Ill., 1984), or as described in detail in Peptides: Synthesis, Structures and Applications (Gutte (ed.), (1995) Academic Press, New York), and Chemical Approaches to the Synthesis of Peptides and Proteins (Lloyd-Willimas, P., Alberico, G., Giralt, E. (eds.) (1997) CRC Press, New York). By using standard peptide synthesis methodology, it would be possible to substitute unnatural amino acids, such as D-amino acids, for natural amino acids to enhance the stability or efficacy of the peptide in a manufactured product. The full-length oligopeptides may be synthesized as one unit wherein amino acids are added one at a time until full length oligopeptide is obtained, or tri-peptide monomers may be synthesized which are then formed into the full-length oligopeptides by fragment condensation (as described, for example by Rinnova, et al. (Lett. Peptide Science (1999) 6:15-22) or by polymerization.

Polymerization of monomeric tri-peptide units into peptide polymers may be carried out by methods such as those described in The Practice of Peptide Synthesis (Bodanszky, M., and Bodanszky, A. (ed.), (1984) Springer-Verlag, New York), Synthetic Polypeptides (Bamford, C. H.; Elliot, A.; and Hanby, W. E. (ed.), (1956) Academic Press, New York), and Nakajima, B-li, and Nishi, N. (Polymer Journal (1981) 13:183-189). Polymerization conditions can be selected to give the desired molecular mass distribution of peptides (Odian, G., Principles of Polymerization (1991) John Wiley & Sons, Inc., New York).

The peptides of the present invention may also be synthesized by solution-phase synthesis according to methods detailed in Chemical Approaches to the Synthesis of Peptides and Proteins (Lloyd-Willimas, P., Alberico, G., Giralt, E. (eds.) (1997) CRC Press, New York) and The Practice of Peptide Synthesis (Bodanszky, M., and Bodanszky, A. (ed.), (1984) Springer-Verlag, New York). For large-scale peptide synthesis, the shorter the length of the peptide sequence, the more amenable it is to large scale solution-phase synthesis (Andesson, et al. Biopolymers (Peptide Science), (2000) 55:227-250). In one embodiment, the monomeric tri-peptide units would be synthesized by solution-phase synthesis, followed by chain lengthening using fragment condensation or polymerization as described above to obtain full-length oligopeptides.

Recombinant Biosynthesis

The peptides of the present invention may also be synthesized by recombinant methods of synthesis. Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989); and by Silhavy, T. J., Bennan, M. L. and Enquist, L. W., *Experiments with Gene Fusions*, Cold Spring Harbor Laboratory Cold Press Spring Harbor, N.Y. (1984); Ausubel, F. M. et al., *Current Protocols in Molecular Biology*, published by Greene Publishing Assoc. and Wiley-Interscience (1987) and PCR Protocols: Current Methods and Applications, Humana Press, Inc., Totowa, N.J. Methods for recombinant synthesis of the peptides of the invention are also described in U.S. Patent Application 60/496122, which is incorporated herein by reference.

Methods for recombinant synthesis of the peptides of the present invention include the preparation of synthetic genes by, for example, in vitro chemical synthesis of the genes using conventional methods as known in the art. "Synthetic genes" can be assembled from oligonucleotide building blocks that are chemically synthesized using procedures known to those skilled in the art. These building blocks are ligated and annealed to form gene segments that are then enzymatically assembled to construct the entire gene. The oligonucleotides necessary may be determined by back-translating from the amino acid sequence of the peptide being synthesized.

"Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Various commercial synthetic apparatuses are available, such as the automated synthesizer from Applied Biosystems (Foster City, Calif.). Accordingly, the coding sequences can be tailored for optimal gene expression based on optimization of nucleotide sequence to reflect the "codon bias" of the host cell. The skilled artisan is well aware of the codon-bias exhibited by a specific host cell in usage of nucleotide codons to specify a given amino acid. Therefore, when synthesizing a gene for expression in a host cell, it is desirable to design the gene such that its frequency of codon usage approaches the frequency of preferred codon usage of the host cell. The skilled artisan appreciates the likelihood of successful gene expression if codon usage is biased towards those codons favored by the host. Determination of preferred codons can be based on a survey of genes derived from the host cell where sequence information is available. Accordingly, in the instant invention, if *Escherichia coli* were used as the expression host, codon bias for enteric bacteria could be utilized as the basis for synthesizing the nucleic acid sequences encoding the antimicrobial peptide such that optimal peptide expression would be obtained in *E. coli*.

The synthetic genes may comprise, in addition to the peptide sequence, a fusion carrier peptide linked to the sequence encoding the antimicrobial peptide. The fusion carrier peptide may protect the host cell during expression from the toxic effects of the antimicrobial peptide. The fusion carrier peptide may also provide a signal sequence to direct export of an expressed antimicrobial peptide, or it may provide a means for subsequent purification of the expressed peptide.

The peptides may also be synthesized as concatemers within a gene. The term "concatemer" herein refers to multiple copies of a given unit as tandem repeats. The multiple copies (multimers) may be separated by intervening sequences that provide, for example, cleavage sites for post-expression peptide recovery. For example, a gene might comprise multiple copies of the peptide described by Formula I:

$$-[(A)_n\text{-}X\text{-}(A)_n\text{-}X\text{-}(A)_n\text{-}X\text{-}(A)_n]-$$

wherein X represents an intervening sequence between two or more copies of the $(A)_n$ sequence for the antimicrobial peptide.

In order to express the antimicrobial peptide in a suitable host cell, the DNA sequence encoding the peptide is operably linked to a suitable promoter. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The DNA sequence of the peptide may be operably linked to a promoter in a suitable vector, plasmid or cassette. The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The antimicrobial peptide may be expressed from the plasmid in a suitable host, or the gene encoding the peptide may be incorporated into the host's chromosome. Host cells preferred for expression of the instant genes and nucleic acid molecules are microbial hosts that can be found broadly within the fungal or bacterial families and which grow over a wide range of temperature, pH values, and solvent tolerances. For example, it is contemplated that any bacteria, yeast, algae and filamentous fungi will be suitable hosts for expression of the present nucleic acid fragments. Because transcription, translation, and the protein biosynthetic apparatus is the same irrespective of the cellular feedstock, functional genes are expressed irrespective of carbon feedstock used to generate cellular biomass. Large scale microbial growth and functional gene expression may utilize a wide range of simple or complex carbohydrates, organic acids and alcohols, and saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of suitable host strains include, but are not limited to: fungal or yeast species such as *Aspergillus, Trichoderma, Saccharomyces, Pichia, Candida* and *Hansenula*; or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium, Klebsiella, Burkholderia, Sphingomonas, Brevibacterium, Corynebacterium, Mycobacterium, Arthrobacter, Nocardia, Actinomyces* and *Comamonas*.

Microbial expression systems and expression vectors containing regulatory sequences that direct high level expression of foreign proteins are well known to those skilled in the art. Any of these could be used to construct chimeric genes for production any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell, are numerous and familiar to those skilled in the art. Virtually any promoter capable of driving these genes is suitable for the present invention including but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, and npr promoters and various phage promoters useful for expression in *Bacillus*.

Termination control regions may also be derived from various genes native to the preferred hosts. Optionally, a termination site may be unnecessary; however, it is most preferred if included.

Plant Host Systems

The instant invention can also be used to transform a suitable plant host with the gene(s) the antimicrobial oligopeptides. Virtually any plant host that is capable of supporting the expression of an antimicrobial peptide gene will be suitable, however crop plants are preferred for their ease of harvesting and large biomass. Suitable plant hosts will include but are not limited to both monocots and dicots such as soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp.), barley (*Hordeum vulgare*), oats (*Avena sativa*, L), sorghum (*Sorghum bicolor*), rice (*Oryza sativa*), *Arabidopsis*, cruciferous vegetables, melons, carrots, celery, parsley, tomatoes, potatoes, strawberries, peanuts, grapes, grass seed crops, sugar beet, sugar cane, canola, millet, beans, peas, rye, flax, hardwood trees, softwood trees, and forage grasses.

Industrial Production of Recombinant Antimicrobial Peptides

Where commercial production of antimicrobial oligopeptides is desired, a variety of culture methodologies may be applied. For example, large-scale production from a recombinant microbial host may be produced by both batch and continuous culture methodologies.

A classical batch culturing method is a closed system where the composition of the medium is set at the beginning of the culture and not subjected to artificial alterations during the culturing process. Thus, at the beginning of the culturing process the medium is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. The carbon substrates may also comprise, for example, alcohols, organic acids, proteins or hydrolyzed proteins, or amino acids. Additionally the carbon substrate may also be one-carbon substrates such as carbon dioxide or methane for which metabolic conversion into key biochemical intermediates has been demonstrated. In addition to one and two carbon substrates, methylotrophic organisms are also known to utilize a number of other carbon containing compounds such as methylamine and glucosamine, as well as methanol and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK).

Similarly, various species of *Candida* will metabolize alanine or oleic acid (Sulter et al., *Arch. Microbiol.*, 153:485-489 (1990)). Hence, it is contemplated that the source of carbon utilized in the present invention may encompass a wide variety of carbon containing substrates and will only be limited by the choice of organism.

Commercial production of antimicrobial peptides may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

As is well known to those skilled in the art, whole microbial cells can be used as catalyst without any pretreatment such as permeabilization. Alternatively, the whole cells may be permeabilized by methods familiar to those skilled in the art (e.g., treatment with toluene, detergents, or freeze thawing) to improve the rate of diffusion of materials into and out of the cells.

Applications:

Oligopeptides produced by the present invention are effective as antimicrobials and can be employed to kill, inhibit, or prevent the growth or proliferation of microorganisms such as Gram-positive bacteria, Gram-negative bacteria, viruses, and fungi. The oligopeptides of the present invention are effective in antimicrobial compositions for use against disease-causing organisms in humans, animals, aquatic and avian species, and plants. The oligopeptides and compositions thereof can also be used as preservatives or sterilants for articles susceptible to microbial contamination. The oligopeptides of the present invention and compositions thereof can be administered to a target cell or host by direct or indirect application. For example, the oligopeptide may be administered topically, systemically or as a coating. The oligopeptides of the present invention and compositions thereof may also be bound to or incorporated into substrates for their use as antimicrobials of material susceptible to microbial contamination or to reduce microbial contamination of the substrate.

Substrates suitable for the present invention include polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising polymers that contain, or may be functionalized to contain, active groups with which peptides may react. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein immobilization are described in Protein Immobilization (Richard F. Taylor (ed.), Marcel Dekker, N.Y., 1991).

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

Additional substrates suitable for the present invention include artificial (or synthetic) marble. Artificial marbles encompass cultured marble, onyx and solid surface materials typically comprising a resin matrix, said resin matrix comprising one or more fillers. Typically, cultured marble is made of a gel coating of unfilled unsaturated polyester on a substrate of a filled unsaturated polyester. The filler may be calcium carbonate or a similar material. Onyx typically consists of a gel coat of unfilled unsaturated polyester on a substrate of filled unsaturated polyester. The filler in this case is typically alumina trihydrate (ATH). Solid surface materials are typically filled resin materials and, unlike cultured marble or onyx, do not have a gel coat. Corian® material available from E. I. du Pont de Nemours and Company (DuPont), Wilmington, Del., is a solid surface material comprising an acrylic matrix filled with ATH. An additional solid surface DuPont material, known by the brand name Zodiaq®, is described as an engineered stone or artificial granite. Such materials are made from an unsaturated polyester matrix filled with quartz.

The articles of the present invention have antimicrobial oligopeptides of the invention bound to or incorporated into a substrate. The use of antimicrobial peptides for rendering substrates antimicrobial provides many advantages to traditional molecules in that peptides exhibit rapid biocidal activity, broad spectrum activity, reduced environmental toxicity and a reduced likelihood of causing organisms to become resistant. Oligopeptides can be bound to a substrate either physicochemically, or covalently. Physicochemical binding of oligopeptides to the substrate may occur by any one or combinations of the following forces: electrostatic, hydrogen bonding, and Van der Waals. Alternatively, oligopeptides may be bound to the substrate surface by a covalent bond. Additionally, antimicrobial oligopeptides of the present invention can be incorporated into the polymer by mixing with the polymer, for example by dissolving the peptide and the polymer in a common solvent and casting or molding the peptide: polymer mixture into an article.

In one embodiment, the antimicrobial oligopeptide is bound to the substrate by coating a substrate polymer with a solution of the peptide, wherein the peptide is at concentration ranging from about 0.001 to about 20 weight percent. The oligopeptide and the substrate polymer may be shaken at temperatures ranging from about 10° C. to about 100° C. for a period of time ranging from about 10 min to 96 hrs. Preferably the oligopeptide and polymer are shaken at a temperature of from about 25° C. to about 80° C. for a period of time ranging from about 1 hr to about 24 hrs.

In another embodiment, the substrate polymer is primed to generate reactive groups that will bind to the antimicrobial oligopeptide. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous solution of from about 0.001 to about 20 weight percent of the antimicrobial peptide. The peptide and the polymer may be shaken at temperatures ranging from about 10° C. to about 100° C. for a period of time ranging from about 10 min to 96 hrs. Preferably the peptide and polymer are shaken at a temperature of from about 25° C. to about 80° C. for a period of time ranging from about 1 hr to about 24 hrs.

In another embodiment, a commercial substrate polymer containing 1-50% reactive groups is brought into contact with 0.001 to about 20 weight percent of the antimicrobial peptide.

After treatment with the antimicrobial oligopeptide, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise a film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is intended to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptide of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy.

Additional child-oriented articles that benefit through comprising the polymer substrate of the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

In order to impart antimicrobial functionality to the products listed, the product can be treated with an antimicrobial peptide of the invention before it is manufactured, or after, or at any time during manufacture of the product. For example, in making an antimicrobial shower curtain, an antimicrobial peptide of the invention may be bound to or incorporated into the polymer substrate, followed by fashioning a shower curtain from the treated material. Alternatively, treatment of the polymer substrate with an antimicrobial peptide of the invention may be performed after the substrate is made into a shower curtain. It is believed that the antimicrobial properties of the material will not change significantly.

Antimicrobial substrates or articles prepared by methods of the invention exhibit antimicrobial functionality, wherein microbes are killed, or microbial growth is reduced or prevented. Antimicrobial activity of the antimcrobial substrate or article can be determined by using any of a number of methods well known in the art, such as the antimicrobial assay described in Example 2 of the present invention. Additional methods for determining antimicrobial activity are discussed in Tenover et al. (eds.), Manual of Clinical Microbiology, 7$^{th}$ Edition, Section VIII, 1999, American Society for Microbiology, Washington, D.C.

EXAMPLES

The present invention is further defined in the following Examples, in which all parts and percentages are by weight unless otherwise indicated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Materials

4-Hydroxymethylphenoxymethyl (HMP) resin, preloaded HMP resin with various amino acids, and 9-fluorenylmethoxycarbonyl (Fmoc) amino acids with fully protected side chains were purchased from Applied Biosystems (Foster City, Calif.). The lysine side chain was protected by a t-butyloxycarbonyl group (t-Boc). Other reagents used for peptide synthesis included trifluoroacetic acid (Aldrich; Milwaukee, Wis.), piperidine (Aldrich), N-methyl-pyrrolidinone (NMP) (VWR; West Chester, Pa.), 1-hydroxybenzotriazole (HOBt) (Applied Biosystems; Foster City, Calif.) and N-[(1H-benzotriazol-1-yl)(dimethylamino)methylene]-N-methylmethanaminium hexafluorophosphate N-oxide (HBTU) (Applied Biosystems); these chemicals were used without further purification.

In the following examples, "milliliter" is abbreviated "mL", "microliter" is abbreviated "µL", "hour(s)" is abbreviated "hr(s)", "minute(s)" is abbreviated "min(s)", and "degrees Centigrade" is abbreviated "° C.".

Example 1

Peptide Synthesis

All peptides were synthesized using standard solid-phase peptide synthesis methodology. The peptides were synthesized using an Applied Biosystems 433A (ABI 433A) Peptide Synthesizer, using 9-fluorenylmethoxycarbonyl (Fmoc)-protected amino acids. Lysine side chains were protected by t-Boc or benzyloxylcarbonyl (CBZ). For peptides with C-terminal carboxylic acids, pre-loaded 4-hydroxymethylphenoxymethyl (HMP) resins loaded with the desired Fmoc-protected amino acids were used. For peptides with C-terminal amides, an Fmoc-amide resin (Applied Biosystems) was used. For the synthesis of peptides with protecting group(s) on the side chain, an acid labile resin was used. For example, 4-hydroxymethyl-3-methoxyphenoxybutyric acid resin, (HMPB-BHA) (NovaBiochem, Darmstadt, Germany) was used for the synthesis of protected peptide fragments.

The subsequent amino acids were coupled by in-situ activation of the carboxylic acid group using a dimethylformamide solution of HOBt and HBTU. The peptides were cleaved from the resins by shaking the resins in 95:2.5:2.5 trifluoroacetic acid (TFA):water:triisopropylsilane at room temperature for two hours. The peptides were triturated from cold ether, and collected by filtration. The crude peptides were purified by preparative HPLC (Varian; Palo Alto, Calif.) on a C18 reverse phase column to >95% purity. The purified peptides were analyzed by analytical HPLC and shown to be >97% pure. Electrospray mass spectroscopy was carried out to confirm the composition and molecular mass of the peptides.

Example 2

Antimicrobial Assay

The minimal inhibitory concentration (MIC) for the peptides was determined in sterile microtiter plates in a final volume of 200 µL using Trypticase Soy Broth (TSB; Difco Laboratories, Detroit, Mich.) as the growth medium. Serial two-fold dilutions of the peptide stock were made in the plate wells such that concentrations ranged from 512 to 2 µg/mL in a volume of 100 µL. Each well was then inoculated with 100 µL of a dilute suspension of bacteria in TSB yielding a final concentration of $1 \times 10^4$ bacteria/mL. The final peptide concentrations ranged from 1 mg/mL to 256 µg/mL. The assay plates were incubated at 37° C. for 24 hours inside a Bioscreen C microtitre plate reader (Thermo Labsystems; Vantaa, Finland). Optical Density (OD) of the medium at 600 nm was recorded every 20 minutes to monitor cell growth. The lowest concentration of peptide preventing bacterial growth during the 24 hr period was defined as the MIC.

TABLE 1

Antimicrobial activity of oligopeptides vs. *E. coli* ATCC 25922.

| SEQ ID NO. | Peptide | MIC (µg/mL) |
|---|---|---|
| 1 | LKALKALKALKALKR | 64 |
| 2 | LKVLKVLKVLKVLKV | 32 |
| 3 | LKVLKVLKVLKVLKVLKV | 4 |
| 4 | FKAFKAFKAFKAFKA | 128 |
| 5 | FKAFKAFKAFKAFKAFKA | 32 |

Example 3

Synthesis of (LKV) Polymer

A) Synthesis of the Tri-Peptide LK(Boc)V by Solid-Phase Synthesis:

The tri-peptide NH$_2$-LK(Boc)-V—CO$_2$H was synthesized on HMPB-BHA resin using the automated solid phase synthesizer ABI 433A as described above. The protected peptide was cleaved from the resin by shaking with 1% trifluoroacetic acid in dichloromethane for 15 minutes, and the subsequent reaction mixture was filtered into a flask containing 10% pyridine in methanol. This process was repeated five additional times. The filtrates were combined and concentrated in vacuo. The crude peptide was obtained by trituration of the concentrated filtrate with cold ether. The crude peptide was purified by HPLC to >90% purity.

B) Polymerization of LK(Boc)V:

The polymerization was based on the procedure described in Zeng et al. (J. Polym. Sci. Polym. Chem. (1992) 30:1809). The tri-peptide (35 mg) was charged into a round bottom flask, followed by lithium chloride (10 mg), triethylamine (40 mg, 0.40 mmol), and dimethylsulfoxide (0.5 mL). The flask was evacuated, filled with argon, and chilled to 0° C. Diphenylphosphorazide (0.2 mmol) was added, the solution was stirred for 30 minutes, and then stirred further at room temperature for two days. Water (3 mL) was added to the reaction mixture, and a precipitate was formed. The precipitate was collected on a coarse fritted filter, and extracted with ether and methanol. The filtrate layers were separated, and the ether layer concentrated in vacuo, dissolved in water, and lyophilized to yield white powder (17 mg). The white powder was shaken in 10 ml 95% trifluoroacetic acid/dichloromethane solution for 2 hours at room temperature. The reaction mixture was concentrated in vacuo, and the concentrate was dissolved in water and lyophilized to yield deprotected peptide polymer. The molecular distribution of the polymer samples was determined by size exclusion chromatography (SEC) on an Alliance 2690™ (Waters Corporation; Milford, Mass.) with a Waters 410™ refractive index detector (DRI) and Viscotek Corporation (Houston, Tex.) Model T-60A™ dual detector modul incorporating static right angle light scattering and differential capillary viscometer detectors. The sample was dissolved in 1,1,1,3,3,3-hexafluoro-2-propanol (HFIP) with 0.01 M sodium trifluoroacetate, and analyzed on two gel permeation chromatography (GPC) HFIP MixC styrene-divinyl benzene columns with exclusion limit of $2 \times 10^7$ and 8,000/30 cm theoretical plates from Polymer Laboratories (Amherst, Mass.).

Size exclusion chromatography analysis of the product was as follows: Mn (number averaged molecular weight): 4690; Mw (weight averaged molecular weight): 8710; Mz (z-averaged molecular weight): 14,600.

The crude deprotected polymer demonstrated an MIC of 64 μg/mL against *E. coli* ATCC 25922.

Example 4

Synthesis of (LKV) Polymer

A) Synthesis of the Tri-Peptide LK(Z)V by Solution-Phase Peptide Synthesis:

The tri-peptide may be synthesized by solution-phase peptide synthesis techniques, as outlined in The Practice of Peptide Synthesis (Bodanszky, M., and Bodanszky, A. (1984) Springer-Verlag, N.Y.). For example, a solution of N-ε-CBZ-L-Lysine methyl ester hydrochloride (25 mmol) in water (20 mL) is treated with a solution of potassium carbonate (36 mmol) in water (10 mL) and the mixture is extracted with ether (three times, 25 mL each). The ether extracts are pooled, and dried over magnesium sulfate and the solvent is removed under reduced pressure. The residue is added to a solution of t-Boc-L-leucine (10 mmoL) in dichloromethane (40 mL) followed by the addition of dicyclohexylcarbodiimide (10 mmol). The solution is stirred at room temperature for five hours. The reaction mixture is filtered, and the filtrate is extracted with 1N HCl, 1N KHCO$_3$, water, and dried over magnesium sulphate, and concentrated to yield N-t-Boc-Leu-Lys(CBZ)-COOMe. The dipeptide (10 mmol) is dissolved in methanol (20 mL) and cooled to 0° C. One equivalent of sodium hydroxide (in 1N solution) is added. The solution is stirred at room temperature for two hours. Dilute hydrochloric acid (10 mL, 1N HCl) is added and the methanol is removed in vacuo. The aqueous solution is cooled in an ice-water bath and stirred, and dilute HCl (about 12 mL 1N HCl) is added to acidify the reaction mixture. The reaction mixture is kept at 0° C. for two hours and the precipitate is collected on a filter, washed with water, and dried. The solid (10 mmol) is resuspended in dichloromethane (40 mL), and a solution of L-valine methyl ester (12 mmol) is added, followed by the addition of dicyclohexylcarbodiimide (10 mmol). The solution is stirred at room temperature for five hours. The reaction mixture is filtered, and the filtrate is extracted with 1N HCl, 1N KHCO$_3$, water, and dried over magsium sulphate, and concentrated to yield N-t-Boc-Leu-Lys(CBZ)-Val-COOMe. The tri-peptide (10 mmol) is dissolved in methanol (20 mL) and cooled to 0° C. One equivalent of sodium hydroxide (in 1N solution) is added. The solution is stirred at room temperature for two hours. Dilute hydrochloric acid (10 mL, 1N HCl) is added and the methanol is removed in vacuo. A one molar solution of HCl in acetic acid is added to the aqueous solution, and the solution is stirred at room temperature for two hours. The resulting solution is lyophilized to a powder. The crude tri-peptide is purified by high performance liquid chromatography (HPLC) to yield NH$_2$-Leu-Lys(CBZ)-Val-COOH.

B) The polymerization of the tri-peptide may be carried out as described in Example 3. The resulting polymer (Leu-Lys (CBz)-Val)$_n$ may be hydrogenated as described, for example, in The Practice of Peptide Synthesis (Bodanszky, M., supra, p. 153) to yield the deprotected polymer (Leu-Lys-Val)$_n$.

Example 5

Hemolysis Assay

The experimental procedure was based, in part, upon O'Leary et al. (ASTM Standard F756-93, Assessment of hemolytic properties of materials, ASTM (1969)), and United States Pharmacopeia, 24$^{th}$ Edition (United States Pharmacopeial Convention, Inc., Rockville, Md., (2000)). The presence of hemolytic material in contact with blood may lyse erythrocytes. The hemoglobin liberated is a direct function of the number of erythrocytes hemolyzed. A quantitative determination of partial hemolysis was made by comparing the hemoglobin level as determined spectrophotometrically in the samples containing test peptide to hemoglobin liberated under control conditions of 0% and 100% hemolysis.

An aliquot of human blood (0.08 mL) was added to each of the test peptide or control substance tubes; the concentration of test peptide was 10 μM. The tubes were sealed, gently inverted, and incubated under static conditions (no agitation) for four hours at 37±2° C. At the end of the incubation period, the tubes were centrifuged at approximately 100×g for 15 minutes at room temperature. An aliquot of each supernatant was transferred to clean spectrophotometer cuvettes and the OD was read at a wavelength of 545 nm. The hemolysis was determined as follows:

Hemolytic index (%)=Replicate Mean OD test sample–Group Mean OD negative control×100 Group Mean OD 100% hemolysis control–Group Mean OD negative control The results are shown in Table 2.

TABLE 2

Hemolytic Index of Peptides.

| SEQ. ID | PEPTIDE | HEMOLYTIC INDEX |
|---|---|---|
| 1 | LKALKALKALKALKR | 0-2 |
| 2 | LKVLKVLKVLKVLKV | 0-2 |
| 3 | LKVLKVLKVLKVLKVLKV | 0-2 |
| 4 | FKAFKAFKAFKAFKA | 0-2 |
| 5 | FKAFKAFKAFKAFKAFKA | 0-2 |
| 6 | KGLKKLLKLLKKLLKL | 20-40 |

Example 6

Antimicrobial Peptide Immobilization On Polyester

Polyester fabric (poly(ethylene terephthalate)) is immersed in a 10% sodium hydroxide solution for 90 min and is then washed with deionized water. The fabric is treated with a 10% hydrogen chloride solution for 20 min, washed with deionized water, and air-dried. The fabric is extracted three times with methylene chloride.

The fabric (100 mg) is weighed into a 20 mL vial. Oligopeptide (SEQ ID NO:114) (10 mg) in 5.5 mL of 50 mM sodium phosphate buffer (pH 6.2) is added to the vial. The mixture is shaken at 70° C. for 16 hrs. The mixture is allowed to cool to room temperature for 20 min, and the excess solution is decanted. The fabric is washed with distilled deionized water (4×10 mL with 15 min agitation), and dried in an oven at 90° C. for 30 min.

Example 7

Antimicrobial Peptide Immobilization On Silk

Silk fiber is extracted three times with methylene chloride prior to use. Oligopeptide (SEQ ID NO:1) (10 mg) and silk fiber (100 mg) are suspended in 5.5 mL of 50 mM sodium phosphate buffer at pH 6.2. The mixture is shaken at 70° C. for 16 hrs. The mixture is allowed to cool to room temperature for 20 min, and then the excess solution is decanted. The fabric is washed with distilled, deionized water (4×10 mL with 15 min agitation), dried in an oven at 90° C. for 30 min, and air dried at room temperature.

Example 8

Antimicrobial Peptide Immobilization On EUPERGIT® Resin

The matrix of EUPERGIT® is a copolymerisate of methacrylamide, N,N'-methylene-bis(methacrylamide) and monomers containing oxirane groups. The oxirane groups function as the reactive components and covalently bind proteins or peptides via their amino and sulfhydryl groups.

EUPERGIT® resin (100 mg EUPERGIT®, Sigma, 150 μm particle size) is charged into a polypropylene vial. Oligopeptide (10 mg) in 1 mL of 1 M phosphate buffer (pH 7.7) is added to the dry resin, followed by the addition of 1.5 mL of 1.0 M sodium phosphate buffer (pH 7.7). The mixture is shaken on a laboratory rotator at room temperature for 15 hr. The vial is centrifuged and the supernantant is decanted. Phosphate buffer (0.1M (pH 7.7); 1.5 mL) is added to the resin; the resin is shaken for 30 min and then centrifuged and decanted. This washing procedure is repeated two additional times. The washed resin is then shaken with a 20% ethanolamine solution in 1.0 M phosphate buffer (pH 7.7) at room temperature overnight. The resin is then washed four times with 0.1 M phosphate buffer (pH 7.7), followed by washing with water (4×).

Example 9

Antimicrobial Peptide Immobilization On Polyurethane

Polyether polyurethane (400 mg, Elasthane™ 75 D, The Polymer Technology Group, Berkeley, Calif.) is dissolved in 0.5 mL of dimethylformamide. To this mixture is added 20 mg of oligopeptide. The mixture is agitated on a vortexer, and the solution is drawn over a glass plate to form a polyurethane film.

What is claimed is:

1. An antimicrobial oligopeptide comprising monomeric tri-peptide units according to:

$$(XZX)_n;\quad\text{Formula (IV)}$$

wherein:

X is a hydrophobic amino acid independently selected from the group consisting of Leu and Ala, with the proviso that only one Ala residue is permitted per monomeric tri-peptide unit;

Z is a cationic amino acid independently selected from the group consisting of Lys, Orn, and Dab; and n=5 to 100 and wherein the antimicrobial oligopeptide exhbits antimicrobial activity and low hemolytic activity.

2. An antimicrobial oligopeptide of claim 1, wherein Z is Lys.

3. The antimicrobial oligopeptide of claims 1, wherein n=5 to 50.

4. The antimicrobial oligopeptide of claims 1, wherein n=5 to 10.

5. The antimicrobial oligopeptide of claims 1, wherein the antimicrobial peptide further comprises an additional one to three uncharged or cationic amino acids at the N-terminus, C-terminus, or a combination thereof.

6. The antimicrobial oligopeptide of claims 1, wherein the antimicrobial peptide is modified on the N-terminus with an acetyl group; modified on the C-terminus with an amide; or a combination thereof.

7. The antimicrobial oligopeptide of claim 5, wherein the antimicrobial peptide is modified on the N-terminus with an acetyl group; modified on the C-terminus with an amide; or a combination thereof.

8. An antimicrobial substrate comprising the antimicrobial oligopeptide of claims 1 bound to or incorporated into a substrate.

9. The substrate of claim 8 selected from the group consisting of (i) polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures thereof; (ii) functionalized polymers selected from the polymers of (i); (iii) ceramics; (iv) glass; (v) metal, (vi) metal oxides, and (vii) composites comprising at least one of the polymers of (i) and at least one of the group consisting of (iii), (iv), (v) and (vi).

10. The substrate of claim 9 comprising a functionalized polymer.

11. An article comprising the antimicrobial substrate of claim 8.

12. The article of claim 11 in the form of a film, membrane, laminate, knit fabric, woven fabric, nonwoven fabric, fiber, filament, yarn, pellet, coating, or foam.

13. An article of claim 11 which has been blown, solution cast, laminated, injection molded, extruded, blow molded, thermoformed, knit, woven, or spun.

14. An article of claim 11 selected from the group consisting of a package; a cosmetic; a personal hygiene article; a food containing article; a food processing article; a food delivering article; a cosmetic application; an inhaler; a medical device; a pharmaceutical or diagnostic container or applicator; a food or seed; a baby item; a personal garment; a medical garment; an agricultural item; a household item; and a separation membrane.

15. A process for preparing an antimicrobial substrate or article, the process comprising the steps of:
(a) contacting the substrate or article with a solution comprising the antimicrobial oligopeptide of claim 1; and
(b) optionally drying the substrate or article produced in step (a).

16. A process for preparing an antimicrobial oligopeptide comprising:
(a) synthesizing monomeric tri-peptide units of claim 1; and
(b) synthesizing full-length oligopeptides by fragment condensation or polymerization of the monomeric tri-peptide units.

17. The process of claim 16, wherein step (a) comprises solid-phase synthesis or solution-phase synthesis.

18. A method for killing, inhibiting, or preventing the growth of at least one microbe, the method comprising contacting the microbe with an effective amount of the antimicrobial oligopeptide of claim 1.

19. A method for killing, inhibiting, or preventing the growth of at least one microbe, the method comprising bringing the microbe into contact with the antimicrobial substrate of claim 8.

* * * * *

UNITED STATES PATENT AND TRADEMARK OFFICE
CERTIFICATE OF CORRECTION

PATENT NO. : 7,563,764 B2
APPLICATION NO. : 11/311387
DATED : July 21, 2009
INVENTOR(S) : Helen S. M. Lu Page 1 of 1

It is certified that error appears in the above-identified patent and that said Letters Patent is hereby corrected as shown below:

Claim 2, column 24, line 53, "an antimicrobial oligopeptide" should read --the antimicrobial oligopeptide--.

Claim 3, column 24, line 55, "claims 1" should read --claim 1--.

Claim 4, column 24, line 57, "claims 1" should read --claim 1--.

Claim 5, column 24, line 59, "claims 1" should read --claim 1--.

Claim 6, column 24, line 64, "claims 1" should read --claim 1--.

Claim 8, column 25, line 6, "claims 1" should read --claim 1--.

Signed and Sealed this

Twenty-second Day of September, 2009

David J. Kappos
*Director of the United States Patent and Trademark Office*

SEQUENCE LISTING

```
<160> NUMBER OF SEQ ID NOS: 11

<210> SEQ ID NO 1
<211> LENGTH: 15
<212> TYPE: PRT
<213> ORGANISM: artificial sequence
<220> FEATURE:
<223> OTHER INFORMATION: Description of artificial sequence: Synthesized
      antimicrobial peptide

<400> SEQUENCE: 1

Leu Lys Ala Leu Lys Ala Leu Lys Ala Leu Lys Ala Leu Lys Arg
1               5                   10                  15

<210> SEQ ID NO 2
<211> LENGTH: 15
<212> TYPE: PRT
<213> ORGANISM: artificial sequence
```

```
<220> FEATURE:
<223> OTHER INFORMATION: peptide

<400> SEQUENCE: 2

Leu Lys Val Leu Lys Val Leu Lys Val Leu Lys Val Leu Lys Val
1               5                   10                  15

<210> SEQ ID NO 3
<211> LENGTH: 18
<212> TYPE: PRT
<213> ORGANISM: artificial sequence
<220> FEATURE:
<223> OTHER INFORMATION: Description of artificial sequence: Synthesized
      antimicrobial peptide

<400> SEQUENCE: 3

Leu Lys Val Leu Lys Val Leu Lys Val Leu Lys Val Leu Lys Val Leu
1               5                   10                  15

Lys Val

<210> SEQ ID NO 4
<211> LENGTH: 15
<212> TYPE: PRT
<213> ORGANISM: artificial sequence
<220> FEATURE:
<223> OTHER INFORMATION: Description of artificial sequence: Synthesized
      antimicrobial peptide

<400> SEQUENCE: 4

Phe Lys Ala Phe Lys Ala Phe Lys Ala Phe Lys Ala Phe Lys Ala
1               5                   10                  15

<210> SEQ ID NO 5
<211> LENGTH: 18
<212> TYPE: PRT
<213> ORGANISM: artificial sequence
<220> FEATURE:
<223> OTHER INFORMATION: Description of artificial sequence: Synthesized
      antimicrobial peptide

<400> SEQUENCE: 5

Phe Lys Ala Phe Lys Ala Phe Lys Ala Phe Lys Ala Phe Lys Ala Phe
1               5                   10                  15

Lys Ala

<210> SEQ ID NO 6
<211> LENGTH: 16
<212> TYPE: PRT
<213> ORGANISM: artificial sequence
<220> FEATURE:
<223> OTHER INFORMATION: Description of artificial sequence: Synthesized
      antimicrobial peptide

<400> SEQUENCE: 6

Lys Gly Leu Lys Lys Leu Leu Lys Leu Leu Lys Lys Leu Leu Lys Leu
1               5                   10                  15

<210> SEQ ID NO 7
<211> LENGTH: 15
<212> TYPE: PRT
<213> ORGANISM: artificial Sequence
<220> FEATURE:
<223> OTHER INFORMATION: Description of artificial sequence: Synthesized
      antimicrobial peptide

<400> SEQUENCE: 7
```

```
-continued

Leu Leu Ala Arg Leu Leu Leu Ala Arg Leu Leu Leu Ala Arg Leu
1               5                   10                  15

<210> SEQ ID NO 8
<211> LENGTH: 12
<212> TYPE: PRT
<213> ORGANISM: artificial Sequence
<220> FEATURE:
<223> OTHER INFORMATION: Description of artificial sequence: Synthesized
      antimicrobial peptide

<400> SEQUENCE: 8

Leu Ala Arg Leu Leu Ala Arg Leu Leu Ala Arg Leu
1               5                   10

<210> SEQ ID NO 9
<211> LENGTH: 16
<212> TYPE: PRT
<213> ORGANISM: artificial Sequence
<220> FEATURE:
<223> OTHER INFORMATION: Description of artificial sequence: Synthesized
      antimicrobial peptide

<400> SEQUENCE: 9

Leu Ala Arg Leu Leu Ala Arg Leu Leu Ala Arg Leu Leu Ala Arg Leu
1               5                   10                  15

<210> SEQ ID NO 10
<211> LENGTH: 9
<212> TYPE: PRT
<213> ORGANISM: artificial Sequence
<220> FEATURE:
<223> OTHER INFORMATION: Description of artificial sequence: Synthesized
      peptide without antimicrobial properties

<400> SEQUENCE: 10

Ala Arg Leu Ala Arg Leu Ala Arg Leu
1               5

<210> SEQ ID NO 11
<211> LENGTH: 12
<212> TYPE: PRT
<213> ORGANISM: artificial Sequence
<220> FEATURE:
<223> OTHER INFORMATION: Description of artificial sequence: Synthesized
      peptide without antimicrobial properties

<400> SEQUENCE: 11

Ala Arg Leu Ala Arg Leu Ala Arg Leu Ala Arg Leu
1               5                   10
```